United States Patent
Moszner et al.

(10) Patent No.: US 7,538,172 B2
(45) Date of Patent: May 26, 2009

(54) DENTAL MATERIALS POLYMERIZABLE BY PHOTO-INDUCED RING-OPENING METATHESIS POLYMERIZATION OF CYCLIC OLEFINS

(75) Inventors: Norbert Moszner, Triesen (LI); Alfred Noels, Liège (BE); Lionel Delaude, Liège (BE); Anna Maj, Liège (BE)

(73) Assignee: Ivoclar Vivadent AG, Schaan (LI)

( * ) Notice: Subject to any disclaimer, the term of this patent is extended or adjusted under 35 U.S.C. 154(b) by 247 days.

(21) Appl. No.: 11/172,008

(22) Filed: Jun. 30, 2005

(65) Prior Publication Data

US 2006/0004158 A1  Jan. 5, 2006

(30) Foreign Application Priority Data

Jun. 30, 2004 (EP) .................. 04103088

(51) Int. Cl.
*C08F 32/08* (2006.01)
(52) U.S. Cl. .................. 526/281; 526/348; 526/280; 526/317.1; 526/318
(58) Field of Classification Search ................ 526/348, 526/281, 280, 317.1, 318
See application file for complete search history.

(56) References Cited

U.S. PATENT DOCUMENTS

| | | |
|---|---|---|
| 6,455,029 B1 | 9/2002 | Angeletakis et al. |
| 6,649,146 B2 * | 11/2003 | Angeletakis et al. .......... 424/49 |
| 6,844,409 B2 * | 1/2005 | Angeletakis et al. ........ 526/279 |

FOREIGN PATENT DOCUMENTS

| | | |
|---|---|---|
| EP | 0 796 607 A2 | 3/1997 |
| EP | 0 904 766 A2 | 9/1998 |
| EP | 0 904 767 A2 | 9/1998 |
| EP | 1 025 830 | 8/2000 |
| EP | 1 317 914 | 6/2003 |
| EP | 1 318 162 | 6/2003 |
| WO | WO 95/07310 A1 | 3/1995 |
| WO | WO03/093351 | 11/2003 |

OTHER PUBLICATIONS

Delaude et al., "Visible light induced ring-opening methathesis polymerisation of cyclooctene" Chem. Commun., 986-987 (2001).*
Delaude et al., "Visible Light Induced Ring-Opening Methathesis Polymerisation of Cyclooctene," Chem. Commun. 986-987 (2001).
Delaude et al., "New In Situ Generated Ruthenium Catalysts Bearing N-Heterocyclic Carbene Ligands for the Ring-Opening Metathesis Polymerization of Cyclooctene," Adv. Snyth. Catal. 344(6+7):749-756 (2002).
Furstner and Ackermann, "A Most User-Friendly Protocol for Ring Closing Metathesis Reactions," Chem. Commun. 95-96 (1999).
Hafner et al., "Recent Developments in Ring-Opening Metathesis Polymerization (ROMP)," Chima 50(4):131-134 (1996).
Hafner et al., "One-Component Catalysts for Thermal and Photoinduced Ring Opening Metathesis Polymerization," Angew. Chem. Int. Ed. Engl. 36(19):2121-2124 (1997).
Karlen et al., "Photoinduced Ring Opening Metathesis Polymerization (PROMP) of Strained Bicyclic Olefins with Ruthenium Complexes of the Type [(eta6-arene1)Ru(eta6-arene2)]2+ and [Ru(NC-R)6]2+," J. Polym. Sci. Part A 33:1665-1674 (1995).

* cited by examiner

*Primary Examiner*—Ling-Siu Choi
(74) *Attorney, Agent, or Firm*—Nixon Peabody LLP

(57) ABSTRACT

Dental material being polymerizable by ring-opening metathesis polymerization comprising (i) at lest one ruthenium complex bearing at least one N-heterocyclic carbene ligand or precursors which generate a ruthenium complex bearing at least one N-heterocyclic carbene ligand in situ; and (ii) at least one cyclic olefin capable of metathesis.

63 Claims, No Drawings

DENTAL MATERIALS POLYMERIZABLE BY PHOTO-INDUCED RING-OPENING METATHESIS POLYMERIZATION OF CYCLIC OLEFINS

This invention relates to polymerizable compositions which can be polymerized by visible-light-induced ring-opening metathesis polymerization. These compositions are particularly useful as dental materials for operative and prosthetic dentistry.

An increasing number of dental materials such as dental filling composites, enamel-dentin adhesives, fixation cements, and materials for inlays, veneers, crowns and bridges and nowadays also for trays or dentures are based on visible-light curing materials. The visible-light curing materials show compared to thermal or chemical cured materials some benefits. Visible-light curing materials are usually single-components materials, which can be easily handled and are free of air bubbles. Furthermore, also highly viscous materials can be processed, used without waste and quickly cured by irradiation with visible-light of wavelengths between ca. 400 and 500 nm, depending on the used photo-initiator system (compare: L-A. Linden "Photocuring of Polymeric Dental Materials and Plastic Composite Resins" in J. P. Fouassier, J. F. Rabek. (Ed.), Radiation Curing in Polymer Science and Technology, Elsevier. Applied Science, London New York 1993, 387-466). Most of the visible-light curing dental materials are based on difunctional methacrylates, which show the drawback of a significant volume shrinkage during their polymerization.

One concept for low-shrinking materials is the ring-opening polymerization of cyclic monomers. In this context the ring-opening metathesis polymerization (ROMP) of cyclic monomers is very attractive.

Dental materials which can be polymerized by ROMP are known in the prior art. EP 0 796 607 A2 discloses dental adhesives and coatings on the basis of functionalized polymers which are obtained by ring-opening metathesis polymerization of functionalized norbornene derivatives. ROMP is induced by transition metal carbene catalysts at 15 to 60° C.

EP 0 904 766 A2 discloses dental materials on the basis of cyclic monomers or oligomers and polymers with cyclic groups, which can be cured by ROMP. ROMP can be induced by light.

EP 0 904 767 A2 discloses dental materials on the basis of oligomers and polymers which are obtained by ROMP of suitable norbornene monomers. The dental materials are hardened by radical polymerization.

U.S. Pat. No. 6,455,029 reveals a composition for the use as a dental impression material including a polymerizable telechelic oligomer or polymer curable with a ruthenium carbene complex catalyst by ROMP.

Delaude et al., J. Chem. Soc.; Chem. Commun. (2001), 986, describe the visible light induced ring-opening metathesis polymerisation of cyclooctene, a typical low-strain cyclic olefin, in chlorobenzene. ROMP is induced by ruthenium-arene complexes bearing N-heterocyclic carbene ligands with aryl substituents.

Delaude et al., Adv. Synth. Catal. 344 (2002) 749, describe in situ generated ruthenium catalysts bearing N-heterocyclic carbene ligands for the photoinduced ring-opening metathesis polymerization (PROMP) of cyclooctene in chlorobenzene.

Karlen et al., J. Polym. Sci. Part A, Polym. Chem. 33 (1995) 1665, and Hafner et al., Chimia 50 (1996) 131, investigated the PROMP of strained bicyclic olefins with cationic ruthenium complexes of the type [($\eta^6$-arene$_1$)Ru($\eta^6$-arene$_2$)]$^{2+}$ and [Ru(NC—R)$_6$]$^{2+}$. The reaction was tolerant to a variety of functional groups and worked in protic polar solvents such as water, ethanol or ethanol/water. Irradiation was carried out with UV light.

Hafner et al., Angew. Chem. Int. Ed. Engl. 36 (1997) 2121 extended this work to [(arene)RuCl$_2$PR$_3$] complexes and the corresponding osmium complexes. The ruthenium-based complexes (arene=p-cymene and PR$_3$=PCy$_3$) were found to show higher reactivity for norbornene polymerization than the osmium complexes.

WO 95/07310 discloses compositions on the basis of cyclic olefins which can be polymerized by photochemical ring-opening metathesis polymerization, using catalytic amounts of heat-stable ruthenium or osmium catalysts with at least one photolabile ligand. Irradiation times of up to 8 hours are needed to achieve complete hardening. Alternatively, short irradiation times of 5 to 60 seconds may be combined with heating to temperatures within the range of 50 to 200° C.

Fürstner et al., J. Chem. Soc.; Chem. Commun. 1999, 95, report the photoactivated ring closing metathesis (RCM) of dienes by [(p-cymene)RuCl$_2$PCy$_3$].

It is the object of the present invention to provide polymerizable materials which show only a low volume shrinkage upon polymerization and which can be cured by visible light within a short time period at room temperature.

This object is achieved by polymerizable materials comprising:

(i) at lest one ruthenium complex bearing at least one N-heterocyclic carbene ligand or
    precursors which generate a ruthenium complex bearing at least one N-heterocyclic carbene ligand in situ; and
(ii) at least one cyclic olefin capable of metathesis.

These materials are polymerizable by ring-opening metathesis polymerization. It was found that combining a ruthenium complex bearing at least one N-heterocyclic carbene ligand with cyclic olefins results in materials which can be hardened by short time irradiation with visible light without the need of subsequent thermal heating. These materials are therefore particularly useful as dental materials for intraoral use.

The materials of the present invention preferably comprise a ruthenium complex of the Formula (I)

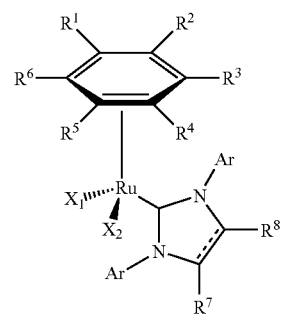

Formula I wherein:

$X_1$ and $X_2$ are independently of each other C$^-$, Br$^-$ or a substituted or unsubstituted phenolate anion;

$R^1$ to $R^6$ are independently of each other hydrogen, $C_1$-$C_6$-alkyl or COOR, R being $C_1$-$C_3$-alkyl;

$R^7$ and $R^8$ are independently of each other hydrogen, $C_1$-$C_{10}$-alkyl, $C_6$-$C_{10}$-aryl, or halogen;

Ar is $C_5$-$C_{10}$-cycloalkyl, substituted or unsubstituted phenyl, or substituted or unsubstituted aryl.

In this formula the dotted line indicates a single bond or, preferably, a double bond.

The optional substituents of the phenolate ion are preferably halogen, preferably chlorine and fluorine.

Preferred definitions of the variables which can be selected independently of each other are:

$X_1$, $X_2$= independently of each other a fully or partially halogenated phenolate anion, in particular a pentalfluorophenolate ion, more preferably $Cl^-$;

$R^1$ to $R^6$= independently of each other hydrogen or $C_1$-$C_3$-alkyl, preferably methyl or isopropyl;

$R^7$, $R^8$= independently of each other $C_1$-$C_4$-alkyl or, more preferably, hydrogen;

Ar = a residue of the Formula (II)

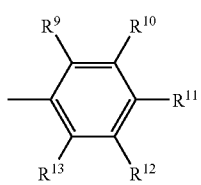

Formula II wherein $R^9$, $R^{10}$, $R^{12}$ and $R^{13}$ are independently of each other H or linear or branched $C_1$-$C_{10}$-alkyl, and $R^{11}$ is H, linear or branched $C_1$-$C_{10}$-alkyl, preferably $C_1$-$C_3$-alkyl, halogen, $C_1$-$C_{10}$-alkoxy, preferably $C_1$-$C_3$-alkoxy, an amino group or a substituted or unsubstituted phenyl group, more preferably methyl.

The residues $R^1$ to $R^6$ may have the same or different meanings, preferably not more than three residues of $R^1$ to $R^6$ are COOR at the same time. It is further preferred that at least two residues of $R^1$ to $R^6$ are alkyl and the remaining residues are hydrogen. Most preferably $R^1$ to $R^6$ and the phenyl group to which they are bound form a hexamethylbenzene, durene (1,2,4,5-tetramethylbenzene), a mono- or dialkylbenzoate or most preferably a p-cymene (p-isopropyltoluene) ligand.

$R^9$ to $R^{13}$ are preferably not all H at the same time. More preferably $R^9$ and $R^{13}$ are $C_1$-$C_4$-alkyl, most preferably methyl, and $R^{10}$ and $R^{12}$ are H, and $R^{11}$ has one of the meanings given above with the exception of hydrogen.

The optional substituents of $R^{11}$ are preferably selected from the group consisting of $C_1$-$C_{10}$ alkyl, preferably $C_1$-$C_3$ alkyl, phenyl, and phenyl substituted by $C_1$-$C_3$-alkyl.

According to a particularly preferred embodiment Ar is 2,4,6-trimethylphenyl (mesityl, Mes). An imidazolidene residue substituted by two mesityl groups ($R^7$=$R^8$=H) is herein abbreviated as IMes.

Particularly preferred are complexes wherein all of the variables have one of the above defined preferred meanings.

Especially preferred is a complex according to Formula (I) wherein $R^1$, $R^2$, $R^4$, $R^5$, $R^7$ and $R^8$ are hydrogen, $R^3$ is methyl, $R^6$ is isopropyl, $X_1$ and $X_2$ are $Cl^-$ and Ar is a residue according to Formula (II) with $R^9$, $R^{11}$ and $R^{13}$ are methyl and $R^{10}$ and $R^{12}$ are H [$RuCl_2$ (p-cymene) (IMes)].

It was found that complexes based on N-heterocyclic carbenes (NHCs) substituted by alkyl groups on both nitrogen atoms showed considerably lesser catalytic activity in the polymerisation of strained olefins than the complexes according to the invention.

According to the invention the preferred catalysts for the visible-light induced ring-opening metathesis polymerization are ruthenium-arene complexes of type 4 bearing a stable N-heterocyclic carbene (NHC) ligand on the metal center. The heterocyclic ligands are substituted by aryl groups, which afford active catalysts, in particular if all the available ortho positions (2 and 6 positions) of the phenyl rings are blocked by alkyl groups, preferably, methyl groups. Biaryl substituted NHC ligands are advantageous, since it is believed that the presence of highly conjugated substituents on the NHC ligand favors the visible light absorption that triggers the photoinitiated polymerization process. Ligands, which are 2,4,6-trisubstituted aryl groups as defined above give particularly efficient catalysts. However, 2,3, (4),5-tetra or -pentaalkyl substituted aryl groups also give efficient catalysts. In the case of 2,6-alkyl substituted derivatives, a substitution in 4 position with a halogen or an alkyl group, or a substituted or unsubstituted aryl group is preferred.

Such species are preferably obtained by reacting e.g. the dichlororuthenium(p-cymene) dimer 1 with a stoichiometric amount of the free carbene. The carbene can be used in preformed form or can be generated in situ by deprotonation of a more stable ionic precursor. Particularly preferred precursors for the carbene are imidazolium and imidazolinium salts (2 or 3). In this formula $Cl^-$ can be replaced by $F^-$, $Br^-$, $I^-$ or $BF_4^-$.

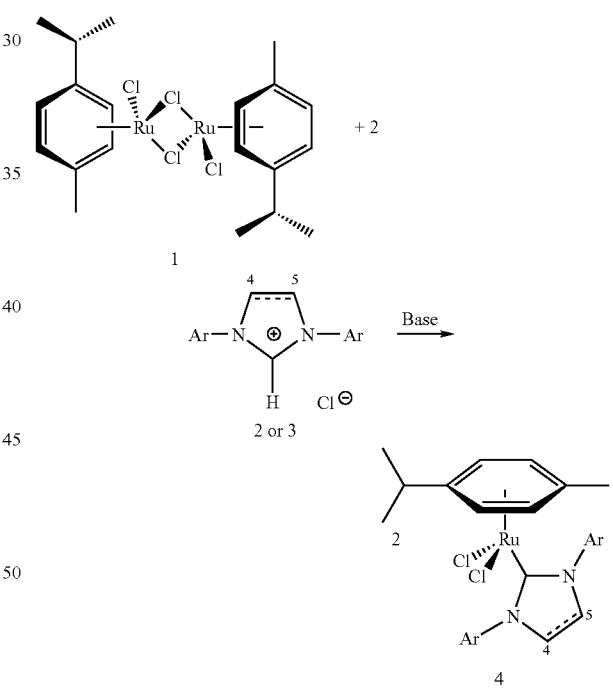

The synthesis of meta- or para-substituted 3,5-di-methyl-biphenyl-4-ylamines can be carried out as described in the following.

Suitable biaryl amines are preferably constructed through a multi-step synthesis involving the ultrasound-promoted Suzuki cross-coupling of various meta- or para-substituted phenyl boronic acids with 4-bromo-2,6-dimethylaniline protected via its trifluoroacetamide. Subsequent deprotection with concentrated aqueous hydrochloric acid, followed by neutralization with barium hydroxide gives the meta- orpara-substituted 3,5 -dimethylbiphenyl-4-ylamines (5).

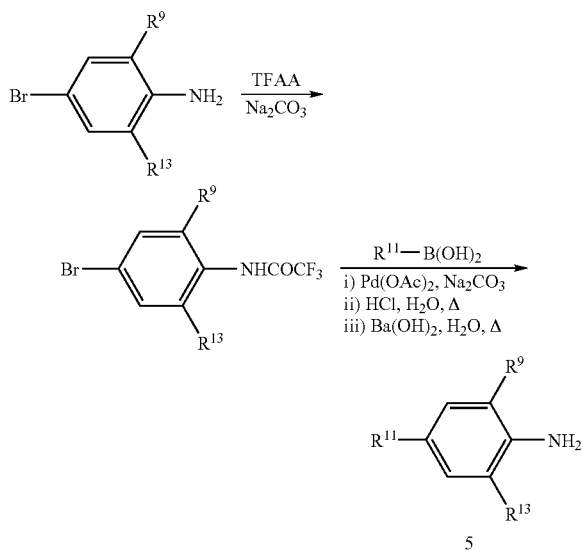

Furthermore, the imidazolium salts (3) bearing two biaryl moieties on the heterocyclic nitrogen atoms can be obtained by condensation of glyoxal with two equivalents of biarylamine followed by cyclization with paraformaldehyde under acidic-conditions. Moreover, the imidazolinium salts (2) bearing two biaryl moieties on the heterocyclic nitrogen atoms, for example, the corresponding imidazolinium chlorides were constructed by reduction of diimine into diamine dihydrochloride and then cyclization with triethyl orthoformate.

These imidazoli(ni)um chlorides can serve as ligand precursors for catalytic systems generated in situ. In that case, complexes of type 4 are formed in the reaction medium by mixing dichlororuthenium(p-cymene) dimer, an imidazoli(ni)um salt, and a base.

Another way is to use imidazolium salts of type 3 and imidazolinium salts of type 2 for the synthesis of preformed ruthenium complexes of type 4. The imidazoli(ni)um salts are first deprotonated in the presence of inorganic bases like sodium hydride, potassium tert-butoxide or potassium bis(trimethylsilyl)amide. The corresponding free NHCs are isolated and react with e.g. $[RuCl_2(p\text{-cymene})]_2$ to afford complexes of type 4 in the second discrete step.

An advantage of the catalyst precursors is their good air stability.

The cyclic olefins (ii) capable of metathesis can be mono- or polycyclic ring systems, for example having 2 to 5 rings, which are unsubstituted or substituted and can contain heteroatoms, for example N, O, Si, P or S, in one or more rings, and may be fused to aromatic or heteroaromatic rings. The cyclic rings preferably contain 4, 5 or 7 to 12, preferably 7 to 10 carbon atoms and 0 to 5, preferably 0, 1 or 2 heteroatoms.

In a preferred embodiment the cyclic olefin (ii) is a strained monocyclic olefin with 4, 5 or 7 to 12, preferably 7 to 10 carbon atoms. Preferred strained monocyclic olefins are cyclobutene, cyclopentene, cycloheptene or $C_9$-$C_{12}$-cycloalkenes.

In another preferred embodiment the cyclic olefin (ii) is a strained polycyclic ring system with at least one endocyclic double bond. Preferred strained polycyclic ring systems are polycyclic cycloolefins such as norbornene (bicyclo[2.2.1]heptene) or norbornene derivatives, in particular endo, exo-2,3-dicarboethoxynorbornene, endo, exo-2,3-dicar-

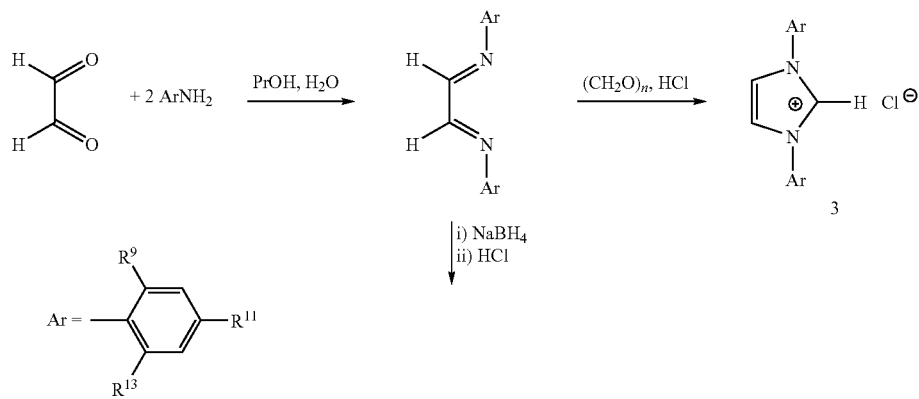

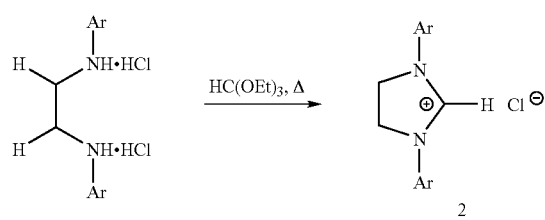

bomethoxynorbomene, 5-norbomen-2-yl acetate and more preferably norbomene derivatives, according to the formulae III or IV

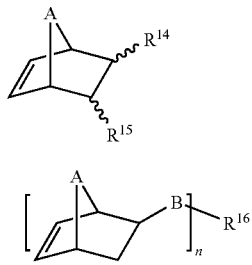

Formula III

Formula IV wherein:
A is O, S or a saturated or unsaturated $C_1C_{20}$-residue, containing 0-5 hetero atoms of the elements N, O, Si, P, S and 0-5 carbonyl groups;
$R^{14}$, $R^{15}$ are independently of each other H or a saturated or unsaturated $C_1C_{30}$-residue, containing 0-10 hetero atoms of the elements N, O, Si, P, S, F and 0-10 carbonyl groups; —COOR', —OR' or —SiR', R' being $C_1$-$C_3$-alkyl or phenyl, or, together with the carbon atoms to which they are bound, form an alicyclic or aromatic, monocyclic or polycyclic residue with 4 to 12 carbon atoms;
n is 2 to 4;
B is a functional linking unit, such as O, S, —CO—O—, —CO—NH— or —O—CO—NH—, —Si(R")$_2$-, or —Si(R")$_2$—O$_{13}$, R" being $C_1$-$C_3$-alkyl, and
$R^{16}$ is n-times substituted $C_1$-$C_{15}$-alkylene, $C_4$-$C_{12}$-cycloalkylene, $C_6$-$C_{14}$-arylene, $C_7$-$C_{20}$-alkylenearylene, —Si(R'")$_{4-n}$', R'" being $C_1$-$C_3$-alkyl, or $SiO_2$.

The norbornene or norbornene derivative may be substituted by 1 or more, preferably 1 or 2 functional groups, which are preferably selected from the group consisting of ester, ether, halogen, alcohol, nitrile, unsubstituted, monosubstituted or disubstituted amide groups. Generally, ester groups with 2 to 5 carbon atoms, monosubstituted amide groups with 2 to 5 carbon atoms, disubstituted amide groups with 3 to 9 carbon atoms, and ether groups with 1 to 4 carbon atoms are preferred.

Particularly preferred monomers are:

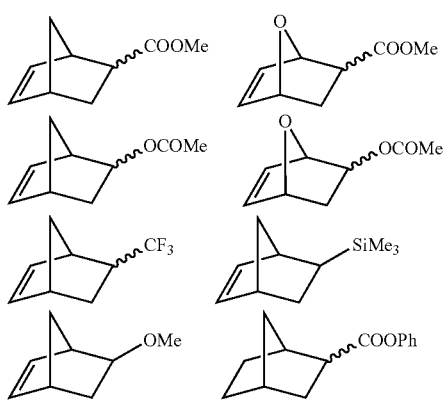

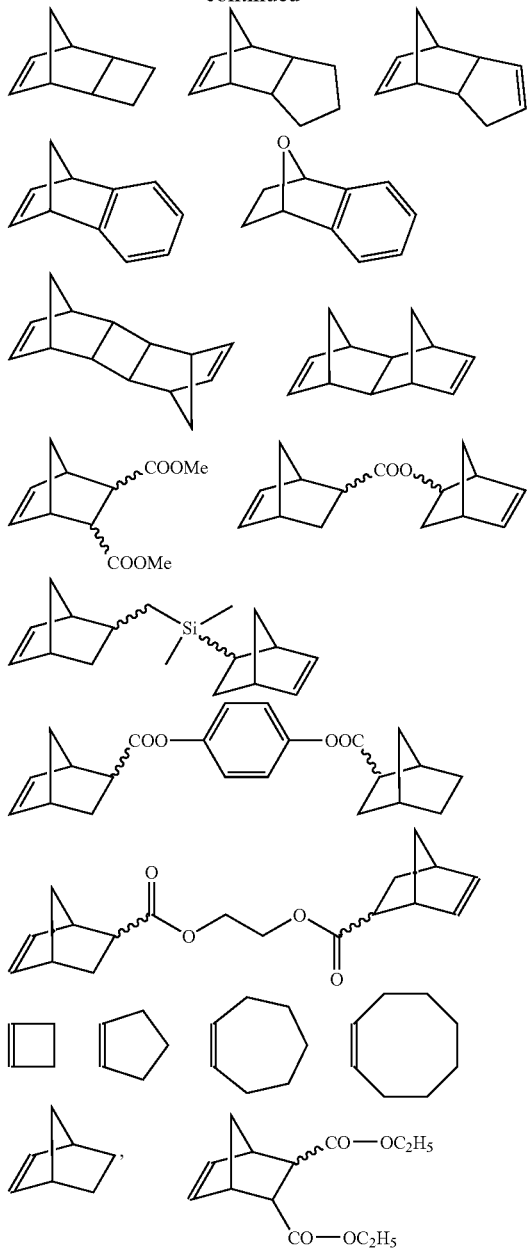

For B=—Si(R")$_2$—O— and $R^{16}$=$SiO_2$ the strained polycyclic ring system is bound to silica to give a compound according to Formula V:

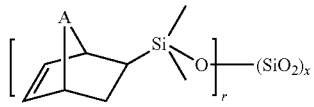

Formula V wherein
r=1
x=1 to 50, more preferably 20-50
and wherein A is preferably —CH$_2$—.

Mixtures of different cyclic monomers as defined above can also be used.

In addition, the previous monomers can be mixed with co-monomers (iii), preferably conventional mono- or difunctional (meth)acrylates, for example, methyl, ethyl, butyl, phenyl or benzyl (meth)acrylate, ethylene, diethylene or triethylene glycol di(meth)acrylate or 1,10-decandiol di(meth)acrylate.

The materials of the present invention preferably also comprise a filler (iv). Preferred fillers according to the invention are spherical inorganic fillers with a mean particle size of 5.0 to 800 nm, preferably of 20-300 nm, for example, fumed silica, precipitated silica, or mixed oxides from $SiO_2$, $ZrO_2$ and/or $TiO_2$ or other oxides, for example of the elements Ta, Yb, La or Ce, as well as macro-fillers having a particle size of 0.4 µm to 10 µm or mini-fillers having a particles size of 5 nm to 100 nm, such as quartz, glass ceramic or glass powder with an average particle size of 0.4 to 10 µm, as well as X-ray-opaque fillers, such as ytterbium trifluoride. Glass or carbon fibres can also be used as fillers. Suitable reinforcing fibres are described, for example, in the "Taschenbuch der Kunststoff-Additive", R. Gächter, H. Müller, Carl Hanser Verlag, Munich and Vienna 1990, pages 617 to 662. Mixtures of different fillers can be used.

The composition according to the invention may contain further additives (v) such as stabilizers, UV absorbers, dyestuffs pigments. In this context stabilizers are substances which prevent premature polymerization and thus above all increase the storage stability.

It is particularly preferred that the compositions of the present invention do not contain solvent. As used herein the term solvent refers to a chemical compound which is liquid at room temperature and serves only to control the reaction or to facilitate handling and processing of the composition, without still being present or necessary in the finished cured composition. If added at all, solvents are usually removed from the composition according to the present invention after polymerization thereof. Liquid reactive monomers which may or may not dissolve the catalyst or other components of the compositions and which are integrated in the polymer network upon polymerization are not solvents in this sense.

The materials according to this invention can be used for the preparation of polymerizable compositions for operative and prosthetic dentistry, for example, of filling composites, fixation cements or veneers.

Preferred materials according to the invention comprise:

0.001 to 5 wt. %, preferably 0.01 to 3 wt. %, and particularly preferably 0.1 to 1 wt. %, of a ruthenium complex (i) bearing N-heterocyclic carbene ligands either preformed or generated in situ;

1 to 90 wt. %, preferably 5 to 70 wt. %, and particularly preferably 10 to 50 wt. % cyclic olefin (ii) capable of metathesis;

0 to 50 wt. %, preferably 0 to 30 wt. %, and particularly preferably 0 to 20 wt. % co-monomer (iii), preferably a mono- or difunctional methacrylate;

optionally 1 to 90 wt. %, preferably 10 to 80 wt. %, and particularly preferably 40 to 80 wt. % filler (iv);

0 to 2.0 wt. % additives (v).

Objects and advantages of the invention are further illustrated by the following examples. The particular materials and amounts thereof, as well as other conditions and details, cited in these examples should not be used to unduly limit the invention.

EXAMPLES

Example 1

2,2,2-Trifluoro-N-(4'-tert-butyl-3,5-dimethyl-biphenyl-4-yl)-acetamide,

A two-neck 100 ml round bottom flask equipped with a reflux condenser capped with a three-way stopcock was charged with 4-tert-butylphenylboronic acid (0.841 g, 4.724 mmol), N-(4-bromo-2,6-dimethylphenyl)-2,2,2-trifluoroacetamide (1.3346 g, 4.73 mmol), Pd(OAc)$_2$ (45 mg, 0.2 mmol), and Na$_2$CO$_3$ (1.009 g, 3.53 mmol). The reactor was purged of air (three vacuum/argon cycles) before degassed methanol (50 ml) was added. The reaction flask was placed in an ultrasound bath for 4.5 h. The solution was filtered on celite and evaporated. The residue was dissolved in 20 ml of CHCl$_3$ and washed twice with water. The organic layer was dried over MgSO$_4$, filtered and evaporated. The crude product was recrystallized from a CHCl$_3$/hexane mixture to afford 2,2,2-trifluoro-N-(4'-tert-butyl-3,5-dimethyl-biphenyl-4-yl)-acetamide as a white grey solid in 74% yield. $^1$H NMR (CDCl$_3$): δ=1.36 (s, 9H, C(CH$_3$)$_3$); 2.28 (s, 6H, ortho-CH$_3$); 7.30-7.31 (d, 2H, CH$_{ar}$); 7.44-7.50 (m, 4H, CH$_{ar}$).

Example 2

4'-tert-Butyl-3,5-dimethyl-biphenyl-4-ylamine

A 250 ml round bottom flask was charged with 5.06 mmol (1.768 g) of 2,2,2-trifluoro-N-(4'-tert-butyl-3,5-dimethyl-biphenyl-4-yl)-acetamide, water (10 ml), and concentrated hydrochloric acid (10 ml). The mixture was heated to reflux for 17 h. The solution was allowed to cool to ambient temperature before it was evaporated to dryness. The residue was refluxed with Ba(OH)$_2$.8H$_2$O (9 g) in 100 ml of water for 1.5 h and then cooled to room temperature. This aqueous solution was extracted three times with 20 ml of CHCl$_3$. The organic layer was dried over MgSO$_4$, filtered, evaporated and dried under vacuum. The resulting brown precipitate of 4'-tert-butyl-3,5-dimethyl-biphenyl-4-ylamine was obtained in 69% yield. $^1$H NMR (CDCl$_3$): δ=1.37 (s, 9H, C(CH$_3$)$_3$); 2.27 (s, 6H, ortho-CH$_3$); 7.30-7.31 (d, 2H, CH$_{ar}$); 7.44-7.50 (m, 4H, CH$_{ar}$). $^{13}$C NMR (CDCl$_3$): δ=18.3 (ortho-CH$_3$); 31.4 (CH$_3$); 34.6 (C(CH$_3$)$_3$); 125.8 (CH$_{ar}$); 126.8 (CH$_{ar}$); 127.2 (CH$_{ar}$); 135.5 (CH$_{ar}$); 137.3 (CH$_{ar}$); 141.4 (CH$_{ar}$); 150.7 (CH$_{ar}$).

Example 3

Glyoxal-bis(4'-tert-butyl-3,5-dimethyl-biphenyl)imine

A mixture of glyoxal (0.307 g of a 40% aqueous solution) in 5 ml of 2-propanol and 2.5 ml of water was slowly added to 4'-tert-butyl-3,5-dimethyl-biphenyl-4-ylamine (1.1 g, 4.34 mmol) in 15 ml of 2-propanol. The reaction mixture was stirred for 3 days at room temperature. The resulting suspension was filtered with suction and the precipitate was rinsed with water (5 ml). It was dried under an IR lamp. The glyoxal-(bis(4'-tert-butyl-3,5-dimethylbiphenyl)imine was obtained as a yellow powder in 71% yield. $^1$H NMR (CDCl$_3$): δ=1.37 (s, 18H, C(CH$_3$)$_3$); 2.26 (s, 12H, ortho-CH$_3$); 7.33 (s, 4H, CH$_{ar}$); 7.45-7.47 (d, 4H, CH$_{ar}$); 7.53-7.55 (d, 4H, CH$_{ar}$); 8.19

(s, 2H, CH=N), $^{13}$C NMR (CDCl$_3$): δ=18.6 (ortho-CH$_3$); 31.5 (CH$_3$); 34.7° (C(CH$_3$)$_3$); 42.2 (CH$_2$); 125.8 (CH$_{ar}$); 126.7 (CH$_{ar}$); 127.1 (CH$_{ar}$); 137.8 (CH$_{ar}$); 138.1 (CH$_{ar}$); 149.1 (CH$_{ar}$); 150.2 (CH$_{ar}$); 163.6 (CH$_{ar}$).

Example 4

N,N'-Bis (4'-tert-butyl-3,5-dimethyl-biphenyl-4-yl)-ethane-1,2-diamine dihydrochloride A solution of glyoxal-bis(4'-tert-butyl-3,5-dimethylbiphenyl)imine (572 mg, 1.08 mmol) in 25 ml of THF was cooled to 0° C. before 168 mg of sodium borohydride (4.42 mmol) were added in one portion. Then 2 eq. (0.178 ml) of concentrated HCl were added dropwise. The reaction mixture was stirred at 0° C. for 20 min. A 3 M aqueous solution of HCl (40 ml) was then carefully added to the flask, still at 0° C., and the reaction mixture was stirred for 1 h at room temperature. The resulting suspension was filtered with suction and the precipitate was rinsed with a small quantity of water and dried under vacuum. N,N'-Bis(4'-tert-butyl-3,5-dimethyl-biphenyl-4-yl)-ethane-1,2-diamine dihydrochloride was obtained as white yellowish powder in 86% yield. $^1$H NMR (DMSO-d$_6$): δ=1.31 (s, 18H, C(CH$_3$)$_3$); 2.57 (s, 12H, CH$_3$); 3.76 (s, 4H, CH$_2$); 7.44-7.48 (d, 8H, CH$_{ar}$); 7.58-7.60 (d, 4H, CH$_{ar}$), $^{13}$C NMR (DMSO-d$_6$): δ=18.4 (ortho-CH$_3$); 31.0 (CH$_3$); 34.1 (C(CH$_3$)$_3$); 42.2 (CH$_2$); 125.6 (CH$_{ar}$); 135.5 (CH$_{ar}$); 136.1 (CH$_{ar}$); 138.6 (CH$_{ar}$); 150.0 (CH$_{ar}$).

Example 5

1,3-Di(4'-tert-butyl-3,5-dimethylbiphenyl)-imidazolinium chloride

A N,N'-diarylethylenediamine dihydrochloride (1.872 g, 3.09 mmol) was suspended in 50 ml of triethylorthoformate containing 2 drops of formic acid. The mixture was refluxed for two days in an oil bath at 130° C. It was then cooled to 6° C. and the resulting suspension was filtered with suction. The precipitate was rinsed with small portions of Et$_2$O and dried under vacuum. The 1,3-di(4'-tert-butyl-3,5-dimethyl-biphenyl)imidazolinium chloride was obtained as a white powder in 60% yield. $^1$H NMR (CDCl$_3$): δ=1.30 (s, 18H, C(CH$_3$)$_3$); 2.22 (s, 12H, ortho-CH$_3$); 3.82 (s, 4H, CH$_2$); 7.21-7.42 (m, 6H, CH$_{ar}$); 7.95 (s, 1H, im-H$^2$).

Example 6

1,3-Di(4'-tert-butyl-3,5-dimethylbiphenyl)-imidazolium chloride

A two-neck 25 ml round bottom flask equipped with a magnetic stirring bar and capped with a three-way stopcock was charged with paraformaldehyde (146 mg, 4.89 mmol). The reactor was purged of air (three vacuum/argon cycles) before 1.44 ml of a 4 N solution of HCl in dioxane was added. The mixture was stirred and gently warmed until complete dissolution of the solid. A second separate two-neck 25 ml round bottom flask equipped with a magnetic stirring bar and capped with a three-way stopcock was charged with glyoxal-bis(4'-tert-butyl-3,5-dimethylbiphenyl)imine (2.158 g, 4.08 mmol) and purged of air (three vacuum/argon cycles) before 16 ml of dry THF was added. The two mixtures were cooled at 0° C. in an ice-water bath and the acidic paraformaldehyde solution was added dropwise to the diimine solution. A precipitate appeared within 1 h. The resulting suspension was stirred 4 h at room temperature. It was filtered with suction and the precipitate was rinsed with AcOEt and dried under vacuum. The 1,3-di(4'-tert-butyl-3,5-dimethylbiphenyl)imidazolium chloride was obtained as a white grey powder in 65% yield. $^1$H NMR (DMSO-d$_6$): δ=1.34 (s, 18H, C(CH$_3$)$_3$); 2.27 (s, 12H, ortho-CH$_3$); 7.53-7.55 (d, 4H, CH$_{ar}$); 7.69-7.70 (m, 8H, CH$_{ar}$); 8.40 (s, 2H, CH=N); 9.87 (s, 1H, im-H$^2$), $^{13}$C NMR (DMSO-d$_6$): δ=17.3 (ortho-CH$_3$); 31.1 (CH$_3$); 34.4 (C(CH$_3$)$_3$); 42.2 (CH$_2$); 125.6 (CH$_{ar}$); 135.5 (CH$_{ar}$); 136.1 (CH$_{ar}$); 138.6 (CH$_{ar}$); 150.0 (CH$_{ar}$)

Example 7

RuCl$_2$ (p-cymene)-(N,N'-di (4'-tert-butyl-3,5-di-methylbiphenyl)imidazolin-2-ylidene)

A two-neck 100 ml round bottom flask equipped with a magnetic stirring bar and capped with a three-way stopcock was charged with 1.8558 mmol (1.075 g) of 1,3-di(4'-tert-butylbiphenyl)imidazolinium chloride and 1.8558 mmol (370 mg) of potassium bis(trimethylsilyl)amide in a glovebox. Next 20 ml of dry and degassed THF was added under an argon atmosphere. The reaction mixture was stirred for 20 min at room temperature before the solvent was evaporated under vacuum. Crude N,N'-di(4'-tert-butyl-3,5-dimethylbiphenyl)imidazolin-2-ylidene was obtained as a brown precipitate in 88% yield. A mixture of [RuCl$_2$(p-cymene)]$_2$ (0.815 mmol, 499 mg) and 25 ml of dry THF was added to the crude residue under an argon atmosphere. The reaction mixture was stirred for 1.5 h at room temperature before the solvent was evaporated under vacuum in the darkness. RuCl$_2$ (p-cymene)-(N,N'-di(4'-tert-butyl-3,5-di-methylbiphenyl) imidazolin-2-ylidene) was obtained as a brown-red solid in 89% yield. $^1$H NMR (CDCl$_3$): δ=1.25 (s, 6H, (CH$_3$)$_2$CH); 1.30 (s, 18H, C(CH$_3$)$_3$); 2.13 (s, 3H, CH$_3$); 2.30 (s, 12H, ortho-CH$_3$); 2.80-3.00 (m, 1H, CH(CH$_3$)$_2$) 3.87 (s, 4H, CH$_2$); 5.32-5.45 (s, 2H, CH$_{ar}$); 5.53-5.62 (s, 2H, CH$_{ar}$) 7.09-7.47 (m, 12H, CH$_{ar}$)

Example 8

ROMP of Norbornene Using a Visible-Light Lamp

Norbornene (361 mg, 3.834 mmol) was dissolved in 5 ml of PhCl, next 7.51×10$^{-6}$ mol (4.6 mg) of [RuCl$_2$(p-cymene)]$_2$, 1.525×10$^{-2}$ mmol (5.2 mg) of 1,3-dimesitylimidazolium chloride and 3.03×10$^{-2}$ mmol (3.4 mg) of KOtBu were added. The solution was irradiated with high power program (1200 mW/cm$^3$) of blue light emitting Astralis 10 lamp for 120 s. 10 ml of CHCl$_3$ were added to dissolve the reaction mixture and the chloroform solution was slowly added to 500 ml of MeOH to precipitate the polymer. The white polymer was filtered and dried under vacuum. Yield 92%.

The rapid and efficient photopolymerisation of dental resins with minimal light exposure is of critical importance for their successful clinical use. The present invention relates to the polymerisation process at room temperature in open vials under the visible light irradiation of blue light-emitting lamps (Astralis 7, Astralis 10 and Plasma lamp Spectramat lamp). These are lamps often used by dentists and dental technicians. This and the following examples show that materials according to the invention can be cured by short time irradiation which is a significant advantage.

Example 9

ROMP of Neat endo,exo-2,3-dicarboethoxynorbornene Using a Visible-Light Lamp Endo,exo-2,3-dicarboethoxynorbornene (477 mg, 2 mmol) and $8 \times 10^{-6}$ mol (4.9 mg) of [RuCl$_2$(p-cymene)(IMes)] were placed in an open 10 ml glass vial. The reaction mixture was homogenized in an ultrasound bath (5 min at room temperature). The solution was irradiated with high power program of blue light emitting Astralis 10 lamp (1200 mW/cm$^3$) for 120 s. 10 ml of CHCl$_3$ were added to dissolve the reaction mixture and the chloroform solution was slowly added to 500 ml of MeOH to precipitate the polymer. The white polymer was filtered and dried under vacuum. Yield 56%.

Example 10

ROMP of Neat 5-norbornen-2-yl acetate Using a Visible-Light Lamp

5-Norbornen-2-yl acetate (304.4 mg, 2 mmol) and $1.002 \times 10^{-6}$ mol (0.6 mg) of [RuCl$_2$(p-cymene)(IMes)] were placed in an open 10 ml glass vial. The catalyst was well soluble in the monomer. The solution was irradiated with high power program (1200 mW/cm$^3$) of blue light emitting Astralis 10 lamp for 120 s. The reaction mixture became solid during the irradiation time. 10 ml of CHCl$_3$ were added to dissolve the reaction mixture and the chloroform solution was slowly added to 500 ml of MeOH to precipitate the polymer. The white polymer was filtered and dried under vacuum. Yield 99%.

Example 11

ROMP of Neat 5-norbornen-2-yl acetate in Presence of TEGDMA Using a Visible-Light Lamp 5-Norbornen-2-yl acetate (608 mg, 4 mmol), triethylene glycol dimethacrylate (TEGDMA) (6 mg, $2 \times 10^2$ mmol) and $2 \times 10^{-6}$ mol (1.2 mg) of [RuCl$_2$(p-cymene)(IMes)] were placed in an, open 10 ml glass vial. A reaction mixture remained liquid for about 10 min in day light. The solution was irradiated with high power program (1200 mW/cm$^3$) of blue light emitting Astralis 10 lamp for 120 s. The reaction mixture became solid during the irradiation time. 10 ml of CHCl$_3$ were added to dissolve the reaction mixture and the chloroform solution was slowly added to 500 ml of MeOH to precipitate the polymer. The white polymer was filtered and dried under vacuum. Yield 99%.

Example 12

ROMP of Neat 5-norbornen-2-yl acetate Using a Plasma Lamp

5-Norbornen-2-yl acetate (304.4 mg, 2 mmol) and $1.002 \times 10^{-6}$ mol (0.6 mg) of [RuCl$_2$(p-cymene)(IMes)] were placed in an open 10 ml glass vial. The catalyst was well soluble in the monomer. The solution was irradiated with a Plasma lamp. (xenon arc plasma lamp) for 120 s. 10 ml of CHCl$_3$ were added to dissolve the reaction mixture and the chloroform solution was slowly added to 500 ml of MeOH to precipitate the polymer. The white polymer was filtered and dried under vacuum. Yield 74%.

Example 13

Preparation of Composite

5-Norbornen-2-yl acetate (4 g, $2.63 \times 10^{-2}$ mol) and $1.29 \times 10^{-2}$ mmol (7.88 mg) of [RuCl$_2$(p-cymene)(IMes)] were well stirred. Then 6 g of filler mixture containing YbF$_3$ and fumed silica OX-50wsil (with YbF$_3$/OX-50wsil=1.87 g/4.13 g) was added to the reaction mixture. The reaction mixture was stirred for 20 s in a stirring machine. The resin was placed in a mould and irradiated using Spectramat lamp (400W metal halogen bulb, 400-500 nm wavelength range) 4×3 min on both sides. The resulting material had a grey-brown shade and an elastic modulus of 3550 N/mm$^2$. The elastic modulus was determined ccording to the ISO norm 4049.

Example 14

ROMP of Neat endo,exo-2,3-dicarbomethoxynorbornene Using an Astralis 7 Lamp Endo,exo-2,3-dicarbomethoxynorbornene (420.4 mg, 2 mmol) was placed in an open 10 ml glass vial and slightly heated with a heat gun until it became liquid. [RuCl$_2$(p-cymene)(IMes)] (0.6 mg, $1.002 \times 10^{-6}$ mol) was then added. The complex was well soluble in the monomer. The solution was irradiated with high power program of blue light emitting Astralis 7 lamp (750 mW/cm$^2$) for 120 s. The resulting solid material had a brownish tint. 10 ml of CHCl$_3$ were added and the chloroform solution was slowly poured into 500 ml of MeOH to precipitate the polymer. The white polymer was filtered and dried under vacuum. Yield 60%.

Example 15 (Comparative)

ROMP of Neat 5-norbornen-2-yl acetate Using Astralis 7 Lamp and [RuCl$_2$(p-cymene)PCy$_3$] as Catalyst Precursor 5-Norbornen-2-yl acetate (304.4 mg, 2 mmol) and [RuCl$_2$(p-cymene)PCy$_3$] (0.6 mg, $1.002 \times 10^{-6}$ mol; Cy=cyclohexyl) were placed in an open 10 ml glass vial. The catalyst was well soluble in the monomer. The solution was irradiated with high power program (750 mW/cm$^2$) of blue light emitting. Astralis 7 lamp for 120 s. The resulting material had a brownish-orange tint. 10 ml of CHCl$_3$ were added to the resulting liquid material and the chloroform solution was slowly poured into 500 ml of MeOH to precipitate the polymer. The white polymer was filtered and dried under vacuum. Yield 11%.

The phosphine-based complex [RuCl$_2$(p-cymene)PCy$_3$] had been used by Hafner et al., Angew. Chem. Int. Ed. Engl. 1997, for ROMP reactions of norbornene in toluene. The present examples shows that this complex is not suitable for ROMP in the absence of solvent while complexes with N-heterocyclic carbene ligands are highly active (cf. Example 10).

Example 16 (Comparative)

ROMP of Neat
endo,exo-2,3-dicarbomethxynorbornene Using an
Astralis 7 Lamp and [RuCl$_2$(p-cymene)PCy$_3$] as
Catalyst Precursor Endo,exo-2,3-dicarbomethoxynorbornene (420.4 mg, 2 mmol) was placed in an open 10 ml glass vial and slightly heated with a heat gun until it became liquid. [RuCl$_2$(p-cymene)PCy$_3$] (0.6 mg, 1.002×10$^{-6}$ mol) was then added. The complex was well soluble in the monomer. The solution was irradiated with high power program of blue light emitting Astralis 7 lamp (750 mW/cm$^2$) for 120 s. The resulting liquid had an orange tint. After 17 h, the liquid reaction mixture was slowly poured into 500 ml of MeOH but no polymer precipitated. Yield 0%.

In this example [RuCl$_2$(p-cymene)PCy$_3$] was completely inactive while the corresponding N-heterocyclic carbene complex [RuCl$_2$(p-cymene) (IMes)] resulted in a polymerization yield of 60% when tested under identical conditions (Example 14).

Example 17 (Comparative)

ROMP of Neat endo
exo-2,3-dicarboethoxynorbornene Using an Astralis
7 Lamp and [RuCl$_2$(p-cymene)PCy$_3$] as Catalyst
Precursor Endo,exo-2,3-dicarboethoxynorbornene (476 mg, 2 mmol) and [RuCl$_2$(p-cymene)PCy$_3$] (0.6 mg, 1.002×10$^{-6}$ mol) were placed in an open 10 ml glass vial. The catalyst was well soluble in the monomer. The solution was irradiated with high power program of blue light emitting Astralis 7 lamp (750 mW/cm$^2$) for 120 s. The resulting liquid had an orange tint. After 17 h, the liquid reaction mixture was slowly poured into 500 ml of MeOH but no polymer precipitated. Yield 0%.

In this example a different monomer was used than in Example 16. However, still no polymerization could be observed.

Example 18 (Comparative)

ROMP of Neat
endo,exo-2,3-dicarbomethoxynorbornene Using an
Astralis 7 Lamp and [Ru(CH$_3$CN)$_6$](tos)$_2$ as Catalyst
Precursor Endo,exo-2,3-dicarbomethoxynorbornene (420.4 mg, 2 mmol) was placed in an open 10 ml glass vial and slightly heated with a heat gun until it became liquid. [Ru(CH$_3$CN)$_6$](tos)$_2$ (0.7 mg, 1.002×10$^{-6}$ mol; tos=p-toluenesulfonate) was then added. The complex was not soluble in the monomer. The mixture was sonicated in an ultrasound bath for 1 h but no sign of dissolution was observed. The mixture was then irradiated with high power program of blue light emitting Astralis 7 lamp (750 mW/cm$^2$) for 120 s. After 2 h, the resulting liquid material was slowly poured into 500 ml of MeOH but no polymer precipitated. Yield 0%.

The ruthenium complex [Ru(CH$_3$CN)$_6$](tos)$_2$ was found by Mühlebach and coworkers, Journal of Polymer Science: Part A: Polymer Chemistry, Vol. 33, 1665-1674 (1995), to be highly active in the photo-induced ROMP of strained bicyclic olefins in protic polar solvents such as water, ethanol or ethanol/water. The reactions had been initiated by irradiation with a Hg lamp for 15 min. The present example shows that [Ru(CH$_3$CN)$_6$](tos)$_2$ completely failed to initiate polymerization upon irradiation with a dental light source in the absence of solvent. Furthermore, Mühlebach et al. performed the polymerization under argon, i.e. under conditions which are disadvantageous for dental purposes.

Example 19 (comparative)

ROMP of Neat 5-norbornen-2-yl acetate Using an
Astralis 7 Lamp and [Ru(CH$_3$CN)$_6$](tos)$_2$ as Catalyst
Precursor 5-Norbornen-2-yl acetate (304.4 mg, 2 mmol) and [Ru(CH$_3$CN)$_6$](tos)$_2$ (0.7 mg, 1.002×10$^{-6}$ mol) were placed in an open 10 ml glass vial. The catalyst was not soluble in the monomer. The mixture was sonicated in an ultrasound bath for 1 h but no sign of dissolution was observed. The mixture was then irradiated with high power program (750 mW/cm$^2$) of blue light emitting Astralis 7 lamp for 120 s. After 2 h the resulting liquid material was slowly poured into 500 ml of MeOH but no polymer precipitated. Yield 0%.

In this example a different monomer was used than in Example 19. However, still no polymerization could be observed.

Example 20 (Comparative)

ROMP of cyclooctene Using [Ru(CH$_3$CN)$_6$](tos)$_2$ as
Catalyst Precursor

A one-neck 25 ml round bottom flask equipped with a magnetic stirring bar and capped with a three-way stopcock was charged with 7.5×10$^{-6}$ mol (5 mg) of [Ru(CH$_3$CN)$_6$](tos)$_2$. The reactor was purged of air (three vacuum/argon cycles) before dry chlorbenzene (1.25 ml) was added. The solution was warmed to 60° C. in a thermostated oil bath and irradiated by a 40W "cold white" fluorescent tube placed 10 cm away from the Pyrex reaction flask. The catalyst was not soluble in the reaction medium. Cyclooctene (0.25 ml, 0.24 g) was added via syringe. The reaction mixture was stirred for 2 h at 60° C. The resulting liquid material was slowly poured into 500 ml of MeOH but no polymer precipitated. Yield 0%.

In this example cyclooctene was used as monomer but the initiator remained inactive.

The invention claimed is:

1. A dental material being polymerizable by ring-opening metathesis polymerization comprising
   (i) at least one ruthenium complex bearing at least one N-heterocyclic carbene ligand or precursors which generate a ruthenium complex bearing at least one N-heterocyclic carbene ligand in situ;
   (ii) at least one cyclic olefin capable of metathesis; and
   (iii) at least one co-monomer, wherein the ruthenium complex is of the formula Formula I

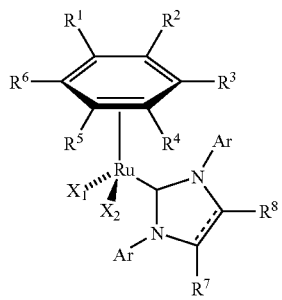

wherein:
X$_1$ and X$_2$ are independently of each other Cl$^-$, Br$^-$ or a substituted or unsubstituted phenolate anion;
R$^1$ to R$^6$ are independently of each other hydrogen, C$_1$-C$_6$-alkyl or COOR, R being C$_1$-C$_3$-alkyl;
R$^7$ and R$^8$ are independently of each other hydrogen, C$_1$-C$_{10}$-alkyl, C$_6$-C$_{10}$-aryl, or halogen;
Ar is C$_5$-C$_{10}$-cycloalkyl, substituted or unsubstituted phenyl, or substituted or unsubstituted aryl, and
the dotted line indicates a single bond or a double bond.

2. The material of claim 1 wherein the variables are:
X$_1$, X$_2$=independently of each other a fully or partially halogenated phenolate anion;
R$^1$ to R$^6$=independently of each other hydrogen or C$_1$-C$_3$-alkyl;
R$^7$, R$^8$=independently of each other C$_1$-C$_4$-alkyl;
Ar=a residue of the Formula (II)

Formula II

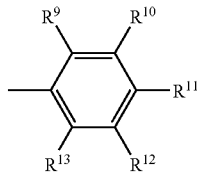

wherein
R$^9$, R$^{10}$, R$^{12}$ and R$^{13}$ are independently of each other H or linear or branched C$_1$-C$_{10}$-alkyl, and
R$^{11}$ is H, linear or branched C$_1$-C$_{10}$-alkyl, halogen, C$_1$-$_{10}$-alkoxy, an amino group or a substituted or unsubstituted phenyl group.

3. The material of claim 2 wherein the substituents of R$^{11}$ are selected from the group consisting of linear or branched C$_1$-C$_{10}$ alkyl, phenyl, phenyl substituted by C$_1$-C$_3$ alkyl.

4. The material of claim 1 comprising [RuCl$_2$(p-cymene)]$_2$ and an imidazolium salt or imidazolium base as the precursors of the catalyst.

5. The material of claim 4 wherein the imidazolium salt is of the formula

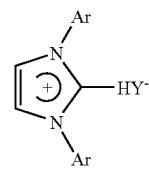

wherein Ar is defined as above and Y$^-$ is F$^-$, Cl$^-$, Br$^-$, I$^-$ or BF$_4^-$.

6. The material of claim 4 wherein the imidazolinium salt is of the formula

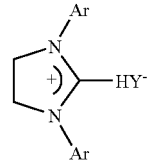

wherein Ar is defined as above and Y$^-$ is F$^-$, Cl$^-$, Br$^-$, I$^-$ or BF$_4^-$.

7. The material of claim 1 wherein the cyclic olefin capable of metathesis is a monocyclic ring or a polycyclic ring system having 2 to 5 rings, which are unsubstituted or substituted, can contain one or more heteroatoms from the group consisting of N, O, Si, P or S, in one or more rings, and can contain fused aromatic or heteroaromatic rings.

8. The material of claim 7, wherein the cyclic rings contain 4, 5 or 7 to 12 carbon atoms and 0 to 5 heteroatoms.

9. The material of claim 8 wherein the cyclic olefin is a strained monocyclic olefin with 4, 5 or 7 to 12 carbon atoms.

10. The material of claim 8 wherein the cyclic olefin is a strained polycyclic ring system with at least one endocyclic double bond.

11. The material of claim 10 wherein the polycyclic olefin is norbornene (bicyclo [2.2.1.]heptene), endo, exo-2 3-dicarboethoxynorbornene, endo, exo-2,3-dicarbomethoxynorbornene, 5-norbornen-2-yl acetate, a norbornene derivative according to formula III or IV Formula III

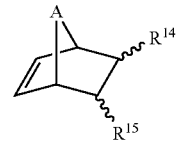

Formula IV

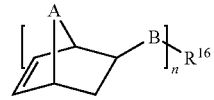

wherein:
A is O, S or a saturated or unsaturated C$_1$-C$_{20}$-residue, containing 0-5 hetero atoms of the elements N, O, Si, P, S and 0-5 carbonyl groups;
R$^{14}$, R$^{15}$ are independently of each other H or a saturated or unsaturated C$_1$-C$_{30}$-residue, containing 0-10 hetero atoms of the elements N, O, Si, P, S, F and 0-10 carbonyl groups; —COOR', —OR'or SiR', R' being C$_1$-C$_3$-alkyl or phenyl, or, together with the carbon atoms to which they are bound, form an alicyclic or aromatic, monocyclic or polycyclic residue with 4 to 12 carbon atoms;
n is 2 to 4;
B is a functional linking unit, such as O, S, —CO—O—, —CO—NH— or —O—CO—NH—, —Si(R")$_2$, or —Si(R")$_2$—O—, R" being C$_1$-C$_3$-alkyl, and
R$^{16}$ is n-times substituted C$_1$-C$_{15}$-alkylene, C$_4$-C$_{12}$-cycloalkylene, C$_6$-C$_{14}$-arylene, C$_7$-C$_{20}$-alkylenearylene, —Si(R''')$_{4-n}$—, R''' being C$_3$-alkyl, or SiO$_2$.

12. The material of claim 11 wherein the norbornene or norbornene derivative is substituted by 1 or more functional groups, which are selected from the group consisting of ester, ether, halogen, alcohol, nitrile, unsubstituted, monosubstituted or disubstituted amide groups.

13. The material of claim 1, wherein the co-monomer (iii) is selected from the group consisting of mono- or difunctional (meth)acrylates, ethylene, diethylene or triethylene glycol di(meth)acrylate and 1,10-decandiol di(meth)acrylate.

14. The material of claim 1 further comprising (iv) filler.

15. The material of claim 14 wherein the filler is a particulate material of spherical inorganic particles with a mean particle size of 5.0 to 800 nm, a macro-filler with an average particle size of 0.4 to 10 μm and/or a mini-filler with an average particles size of 5 to 100 nm.

16. The material of claim 14 wherein the filler is selected from the group consisting of fumed silica, precipitated silica, mixed oxides from $SiO_2$, $ZrO_2$ and/or $TiO_2$ or other oxides, quartz powder, glass ceramic powder, glass powder, ytterbium trifluoride and mixtures thereof.

17. The material of claim 14 comprising glass fibers and/or carbon fibers as a filler.

18. The material of claim 14 further comprising one or more additives (v) selected from the group consisting of stabilizers, UV absorbers, dyestuffs, pigments and mixtures thereof.

19. The material of claim 1 comprising 0.001 to 5 wt.-% ruthenium complex (i);
 1 to 90 wt.-% cyclic olefin (ii) capable of metathesis;
 0 to 50 wt.% co-monomer (iii);
 optionally 1 to 90 wt.-% filler (iv); and
 0 to 2.0 wt.-% additives (v).

20. The material of claim 1 which is substantially free of solvent.

21. A method for the use of the material of claim 1 comprising applying the material of claim 1 to the tooth of a patient as a dental material or incorporating the material of claim 1 in the manufacture of a dental material.

22. The method of use of claim 21 wherein the dental material is material for operative and prosthetic dentistry.

23. The method of use of claim 21 wherein the material is a filling composite, a fixation cement or a veneering material.

24. The material of claim 1 wherein $X_1$, $X_2$=a pentafluorophenolate ion.

25. The material of claim 1, wherein $X_1$, $X_2$=Cl$^-$.

26. The material of claim 1 wherein $R^1$ to $R^6$=methyl or isopropyl.

27. The material of claim 1 wherein $R^7$, $R^8$=hydrogen.

28. The material of claim 1 wherein $R^{11}$ is $C_1$-$C_3$-alkyl.

29. The material of claim 1 wherein $R^{11}$ is $C_1$-$C_3$-alkoxy.

30. The material of claim 7, wherein the cyclic rings contain 7 to 10 carbon atoms.

31. The material of claim 7, wherein the cyclic rings contain 0, 1 or 2 hetero atoms.

32. The material of claim 13, wherein the mono- or difunctional (meth)acrylates are selected from the group consisting of methyl, ethyl, butyl, phenyl, or benzyl (meth)acrylate.

33. A dental material being polymerizable by ring-opening metathesis polymerization comprising
 (i) at least one ruthenium complex bearing at least one N-heterocyclic carbene ligand or precursors which generate a ruthenium complex bearing at least one N-heterocyclic carbene ligand in situ;
 (ii) at least one cyclic olefin capable of metathesis; and
 (iii) a filler, wherein the filler is a particulate material of spherical inorganic particles with a mean particle size of 5.0 to 800 nm, a macro-filler with an average particle size of 0.4 to 10 μm and/or a mini-filler with an average particles size of 5 to 100 nm; and wherein the ruthenium complex is of the formula

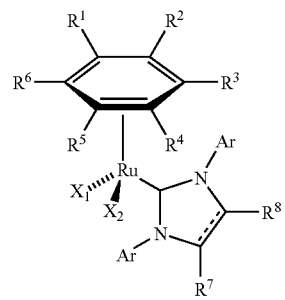

Formula I wherein:
 $X_1$ and $X_2$ are independently of each other Cl$^-$, Br$^-$ or a substituted or unsubstituted phenolate anion;
 $R^1$ to $R^6$ are independently of each other hydrogen, $C_1$-$C_6$-alkyl or COOR, R being $C_1$-$C_3$-alkyl;
 $R^7$ and $R^8$ are independently of each other hydrogen, $C_1$-$C_{10}$-alkyl, $C_6$-$C_{10}$-aryl, or halogen;
 Ar is $C_5$-$C_{10}$-cycloalkyl, substituted or unsubstituted phenyl, or substituted or unsubstituted aryl, and
 the dotted line indicates a single bond or a double bond.

34. The material of claim 33 wherein the variables are:
 $X_1$, $X_2$=independently of each other a fully or partially halogenated phenolate anion;
 $R^1$ to $R^6$=independently of each other hydrogen or $C_1$-$C_3$-alkyl;
 $R^7$, $R^8$=independently of each other $C_1$-$C_4$-alkyl; Ar=a residue of the Formula (II)

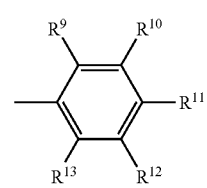

Formula II wherein
 $R^9$, $R^{10}$, $R^{12}$ and $R^{13}$ are independently of each other H or linear or branched $C_1$-$C_{10}$-alkyl, and
 $R^{11}$ is H, linear or branched $C_1$-$C_{10}$-alkyl, halogen, $C_1$-$C_{10}$-alkoxy, an amino group or a substituted or unsubstituted phenyl group.

35. The material of claim 34 wherein the substituents of $R^{11}$ are selected from the group consisting of linear or branched $C_1$-$C_{10}$ alkyl, phenyl, phenyl substituted by $C_1$-$C_3$ alkyl.

36. The material of claim 33 comprising [RuCl$_2$(p-cymene)]$_2$ and an imidazolium salt or imidazolium base as the precursors of the catalyst.

37. The material of claim 36 wherein the imidazolium salt is of the Formula

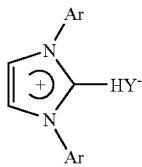

wherein Ar is defined as above and Y⁻ is F⁻, Cl⁻, Br⁻, I⁻ or BF₄⁻.

38. The material of claim 36 wherein the imidazolinium salt is of the formula

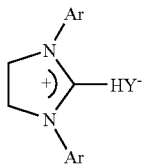

wherein Ar is defined as above and Y⁻ is F⁻, Cl⁻, Br⁻, I⁻ or BF₄⁻.

39. The material of claim 33 wherein the cyclic olefin capable of metathesis is a monocyclic ring or a polycyclic ring system having 2 to 5 rings, which are unsubstituted or substituted, can contain one or more heteroatoms from the group consisting of N, O, Si, P or S, in one or more rings, and can contain fused aromatic or heteroaromatic rings.

40. The material of claim 39, wherein the cyclic rings contain 4, 5 or 7 to 12 carbon atoms and 0 to 5 heteroatoms.

41. The material of claim 40 wherein the cyclic olefin is a strained monocyclic olefin with 4, 5 or 7 to 12 carbon atoms.

42. The material of claim 40 wherein the cyclic olefin is a strained polycyclic ring system with at least one endocyclic double bond.

43. The material of claim 42 wherein the polycyclic olefin is norbornene (bicyclo [2.2.1.]heptene), endo, exo-2,3-dicarboethoxynorbornene, endo, exo-2,3-dicarbomethoxynorbornene, 5-norbornen-2-yl acetate, a norbornene derivative according to formula III or IV

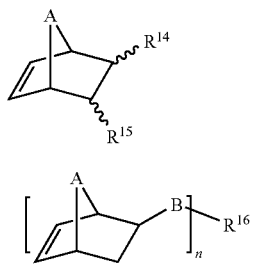

wherein:
A is O, S or a saturated or unsaturated $C_1$-$C_{20}$-residue, containing 0-5 hetero atoms of the elements N, O, Si, P, S and 0-5 carbonyl groups;

$R^{14}$, $R^{15}$ are independently of each other H or a saturated or unsaturated $C_1$-$C_{30}$-residue, containing 0-10 hetero atoms of the elements N, O, Si, P, S, F and 0-10 carbonyl groups; —COOR', —OR' or —SiR', R' being $C_1$-$C_3$-alkyl or phenyl, or, together with the carbon atoms to which they are bound, form an alicyclic or aromatic, monocyclic or polycyclic residue with 4 to 12 carbon atoms;

n is 2 to 4;

B is a functional linking unit, such as O, S, —CO—O—, —CO—NH— or —O—CO—NH—, —Si(R')₂-, or —Si(R")₂—O—, R" being $C_1$-$C_3$-alkyl, and $R^{16}$ n-times substituted $C_1$-$C_{15}$-alkylene, $C_4$-$C_{12}$-cycloalkylene, $C_6$-$C_{14}$-arylene, $C_7$-$C_{20}$-alkylenearylene, —Si(R''')$_{4-n}$—, R'''being $C_1$-$C_3$-alkyl, or SiO₂.

44. The material of claim 43 wherein the norbornene or norbornene derivative is substituted by 1 or more functional groups, which are selected from the group consisting of ester, ether, halogen, alcohol, nitrile, unsubstituted, monosubstituted or disubstituted amide groups.

45. The material of claim 33 further comprising at least one co-monomer (iv).

46. The material of claim 45, wherein the co-monomer (iv) is selected from the group consisting of mono- or difunctional (meth)acrylates, ethylene, diethylene or triethylene glycol di(meth)acrylate and 1,10-decandiol di(meth)acrylate.

47. The material of claim 33 wherein the filler is selected from the group consisting of fumed silica, precipitated silica, mixed oxides from SiO₂, ZrO₂ and/or TiO₂ or other oxides, quartz powder, glass ceramic powder, glass powder, ytterbium trifluoride and mixtures thereof.

48. The material of claim 47 comprising glass fibers and/or carbon fibers as a filler.

49. The material of claim 47 further comprising one or more additives (v) selected from the group consisting of stabilizers, UV absorbers, dyestuffs, pigments and mixtures thereof.

50. The material of claim 33 comprising 0.001 to 5 wt.-% ruthenium complex (i);
1 to 90 wt.-% cyclic olefin (ii) capable of metathesis;
0 to 50 wt.% co-monomer (iv);
optionally 1 to 90 wt.-% filler (iii); and
0 to 2.0 wt.-% additives (v).

51. The material of claim 33 which is substantially free of solvent.

52. A method for the use of the material of claim 33 comprising applying the material of claim 33 to the tooth of a patient as a dental material or incorporating the material of claim 33 in the manufacture of a dental material.

53. The method of use of claim 52 wherein the dental material is material for operative and prosthetic dentistry.

54. The method of use of claim 52 wherein the material is a filling composite, a fixation cement or a veneering material.

55. The material of claim 33 wherein $X_1$, $X_2$=a pentafluorophenolate ion.

56. The material of claim 33, wherein $X_1$, $X_2$=Cl⁻.

57. The material of claim 33 wherein $R^1$ to $R^6$=methyl or isopropyl.

58. The material of claim 33 wherein $R^7$, $R^8$=hydrogen.

59. The material of claim 33 wherein $R^{11}$ is $C_1$-$C_3$-alkyl.

60. The material of claim 33 wherein $R^{11}$ is $C_1$-$C_3$-alkoxy.

61. The material of claim 39, wherein the cyclic rings contain 7 to 10 carbon atoms.

62. The material of claim 39, wherein the cyclic rings contain 0, 1 or 2 heteroatoms.

63. The material of claim 46, wherein the mono- or difunctional (meth)acrylates are selected from the group consisting of methyl, ethyl, butyl, phenyl, or benzyl (meth)acrylate.

* * * * *